(12) United States Patent
Federle et al.

(10) Patent No.: US 9,125,652 B2
(45) Date of Patent: Sep. 8, 2015

(54) DRAPE FOR A SURGICAL MICROSCOPE

(71) Applicant: Carl Zeiss Meditec, Inc., Dublin, CA (US)

(72) Inventors: Dennis Federle, Loveland, OH (US); James J. Laux, Kinnelon, NJ (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 13/627,517

(22) Filed: Sep. 26, 2012

(65) Prior Publication Data

US 2013/0329291 A1  Dec. 12, 2013

Related U.S. Application Data

(60) Provisional application No. 61/539,569, filed on Sep. 27, 2011.

(51) Int. Cl.
*A61B 19/08* (2006.01)

(52) U.S. Cl.
CPC .................................. *A61B 19/081* (2013.01)

(58) Field of Classification Search
CPC .. A61B 19/081; A61B 19/10; G02B 21/0012; G02B 21/0006; G02B 27/006; Y10S 383/907
USPC .......... 359/507, 510; 128/849, 852; 206/305; 600/121; 383/907; 150/154
See application file for complete search history.

(56) References Cited

U.S. PATENT DOCUMENTS

| 3,698,791 | A | 10/1972 | Walchle et al. | |
|---|---|---|---|---|
| 4,564,270 | A * | 1/1986 | Willie | 359/511 |
| 4,975,826 | A * | 12/1990 | Bell | 362/376 |
| 7,182,474 | B2 * | 2/2007 | Fuchs et al. | 359/510 |
| 2002/0151848 | A1* | 10/2002 | Capote et al. | 604/171 |
| 2004/0190140 | A1 | 9/2004 | Bala | |
| 2007/0064309 | A1 | 3/2007 | Luloh et al. | |

OTHER PUBLICATIONS

German Office Action, with translation thereof, for corresponding DE Appl No. 10 2012 018 985.0, dated Jun. 9, 2013.

* cited by examiner

*Primary Examiner* — Thomas K Pham
*Assistant Examiner* — Cara Rakowski
(74) *Attorney, Agent, or Firm* — Fish & Richardson P.C.

(57) ABSTRACT

The disclosure relates to a drape with an opening and an attachment device on the first opening to affix the drape on a surgical microscope. The drape can include a second attachment device arranged on the opening to affix the drape on the surgical microscope.

24 Claims, 6 Drawing Sheets

DRAPE FOR A SURGICAL MICROSCOPE

CROSS-REFERENCE TO RELATED APPLICATIONS

This application claims priority under 35 U.S.C. §119(e)(1) to U.S. Provisional Application No. 61/539,569 filed Sep. 27, 2011, the entire contents of which are incorporated by reference herein.

FIELD

The disclosure relates to a drape with an opening and an attachment device on the opening to affix the drape on a surgical microscope.

BACKGROUND

US 2007/0064309 A1 discloses a drape with a first opening and a first attachment device. In order to attach the drape to a surgical microscope, the opening in the drape is guided under an objective of the surgical microscope via an adapter and the drape is affixed on the adapter by means adhesive strip. Subsequently, the drape can be put over the whole surgical microscope and attached to a support arm by a sterile tape. Hence the adapter is situated outside of the drape during surgery and can subsequently be adjusted. The adhesive strip, by which the drape is attached to the adapter, keeps the drape in its position during the surgery and ensure that the view of the operator is not impeded by the drape. A potential disadvantage of the drape disclosed in US 2007/0064309 A1 is that there cannot be much movement of the adapter and an examination device connected thereto. By way of example, it is difficult, if even possible, to pivot the adapter with the associated examination device out of the beam path of the surgical microscope because a correct positioning of the drape is then no longer ensured.

SUMMARY

The disclosure seeks to provide a drape for a surgical microscope which enables greater movability of various components of a surgical microscope relative to one another.

In one aspect, the drape includes a second attachment device, which is arranged on the first opening for affixing the drape on the surgical microscope. As a result, an option is provided for attaching the drape at a further point on the surgical microscope. In particular, the drape can, via the first attachment device, be affixed to a first component of the surgical microscope and, via the second attachment device, be affixed to a second component, which is designed to be able to move relative to the first component, of the surgical microscope. As a result of attaching the drape to at least two points or two components of the surgical microscope, the drape is, even in the case of relative movement between the two points or two components of the surgical microscope, affixed in the region of the first opening such that undesired displacement or folding of the drape is at least largely prevented.

In one embodiment of the disclosure, the first attachment device extends along a first part of an edge of the first opening. Here, the first attachment device is preferably arranged directly on the first part of the edge of the first opening. However, it can also be positioned at a distance from the first part of the edge of the first opening as long as the geometry of the drape and the surgical microscope ensures that the part of the drape between the first attachment device and the edge cannot be introduced into an observation beam path of the microscope and/or into a workspace of the operator. In other words, a distance between the attachment device and the edge of the drape in the radial direction is preferably smaller than a minimum distance between the attachment device and the observation beam path. As a result of the first attachment device extending along part of the edge of the first opening, the drape can easily be attached to the surgical microscope in the region of the first opening.

In a further embodiment of the disclosure, the first attachment device includes a detachable adhesive connection. As a result of this, a simple and cost-effective option is provided for affixing the drape to the surgical microscope with the aid of a cohesive connection and/or for sealing the interior of the drape from environmental effects.

In a further embodiment of the disclosure, the first attachment device includes a clamping device, by which the drape can be securely clamped to the surgical microscope in the region of the first opening. By way of example, the clamping device is embodied as a spring clip or clip. As a result of this, a simple and cost-effective option is provided for affixing the drape to the surgical microscope with the aid of a force-fit connection and/or for protecting the interior of the drape from environmental effects.

In a further embodiment of the disclosure, the clamping device has a U-shaped holder, which can be inserted into a groove on the surgical microscope. The U-shaped holder preferably has a design that is slightly smaller than the groove such that it has to be slightly bent open during the insertion into the groove. As a result, a spring effect is created, and so friction between the holder and the support face in the groove is increased. Hence, the holder is securely held in the groove a force-fit and interlocking connection. By way of example, the groove can be embodied in a housing of a component of the surgical microscope or at an interface between two components.

In a further embodiment of the disclosure, the second attachment device extends along a second part of the edge of the first opening. Here, the second attachment device is preferably arranged directly on the second part of the edge of the first opening. However, it can also be positioned at a distance from the second part of the edge of the first opening as long as the geometry of the drape and the surgical microscope ensures that the part of the drape between the first attachment device and the edge cannot be introduced into an observation beam path of the microscope and/or into a workspace of the operator. The first part of the edge and the second part of the edge can directly adjoin one another or be arranged at a distance from one another.

In a further embodiment of the disclosure, the first part of the edge and the second part of the edge together extend over less than the totality of the edge of the first opening. In other words, a freely movable section of the edge is arranged between the first part of the edge and the second part of the edge. It is particularly preferred for freely movable sections of the edge to be respectively arranged on both sides of the first part of the edge, which freely movable sections respectively in turn adjoin the second part of the edge. Here, a "freely movable section" should be understood to mean a section of the edge, the alignment of which is not or only insignificantly restricted by the first attachment device and/or the second attachment device. In other words, the first attachment device and the second attachment device are positioned in a spatially separated manner on the first opening such that the first part of the edge and the second part of the edge do not form a common intersection. As a result, a position of the first attachment device relative to the second attachment device can be varied in many or all spatial degrees of freedom.

In a further embodiment of the disclosure, the second attachment device includes a detachable adhesive connection. As a result of this, a simple and cost-effective option is provided for affixing the drape to the surgical microscope with the aid of a cohesive connection and/or for sealing the interior of the drape from environmental effects.

In a further embodiment of the disclosure, the second attachment device includes a clamping device, by which the drape can be securely clamped to the surgical microscope in the region of the first opening. By way of example, the clamping device is embodied as a spring clip or clip. As a result of this, a simple and cost-effective option is provided for affixing the drape to the surgical microscope with the aid of a force-fit connection and/or for sealing the interior of the drape from environmental effects.

In a further embodiment of the disclosure, the second attachment device includes a connection element with a largely rigid design which can be affixed to the surgical microscope at an attachment point. Here, a connection element with a rigid design should be understood to mean an element which, under the effect of its inherent weight and without any external load, largely maintains its shape in any position. After the connection element is fixed to the surgical microscope, a rigid connection is established between the component of the surgical microscope on which the connection element is affixed and the point or the area at which the connection element is attached to the drape. This allows the drape to be carried along in an areal region around the second attachment device in a defined manner when a component of the surgical microscope is displaced.

In a further embodiment of the disclosure, the connection element is embodied as a plate. As a result of this, a solid barrier between the surgical microscope and a workspace of the operator is created in a portion, which firstly reduces the risk of accessories or feed lines of the surgical microscope or sections of the drape projecting into the workspace and secondly makes it more difficult for germs or foreign bodies to pass into the workspace from the interior of the drape.

In a further embodiment of the disclosure, the drape has a second opening. With the aid of the second opening, the drape can easily be attached to the surgical microscope by being put on the latter by virtue of the drape initially being affixed on the surgical microscope in the region of the first opening and subsequently being put over the surgical microscope. This simplifies the assembly of the drape.

In a further embodiment of the disclosure, the drape has an elastic element which is attached to an edge or in the vicinity of an edge of the second opening at at least two different points such that an elastic force can be exerted on the two different points. In particular, the elastic element can also be attached to the drape in a linear fashion along the edge or along sections of the edge of the second opening. By pulling the elastic element it is possible to enlarge an opening area of the second opening such that the drape can easily be pulled over the surgical microscope. As soon as the load is removed from the elastic element, it contracts such that the drape rests against the surgical microscope in the region of the second opening and is held securely.

BRIEF DESCRIPTION OF THE DRAWINGS

In the following text, the disclosure will be explained in more detail on the basis of the drawings, in which.

DETAILED DESCRIPTION

Figure 1:
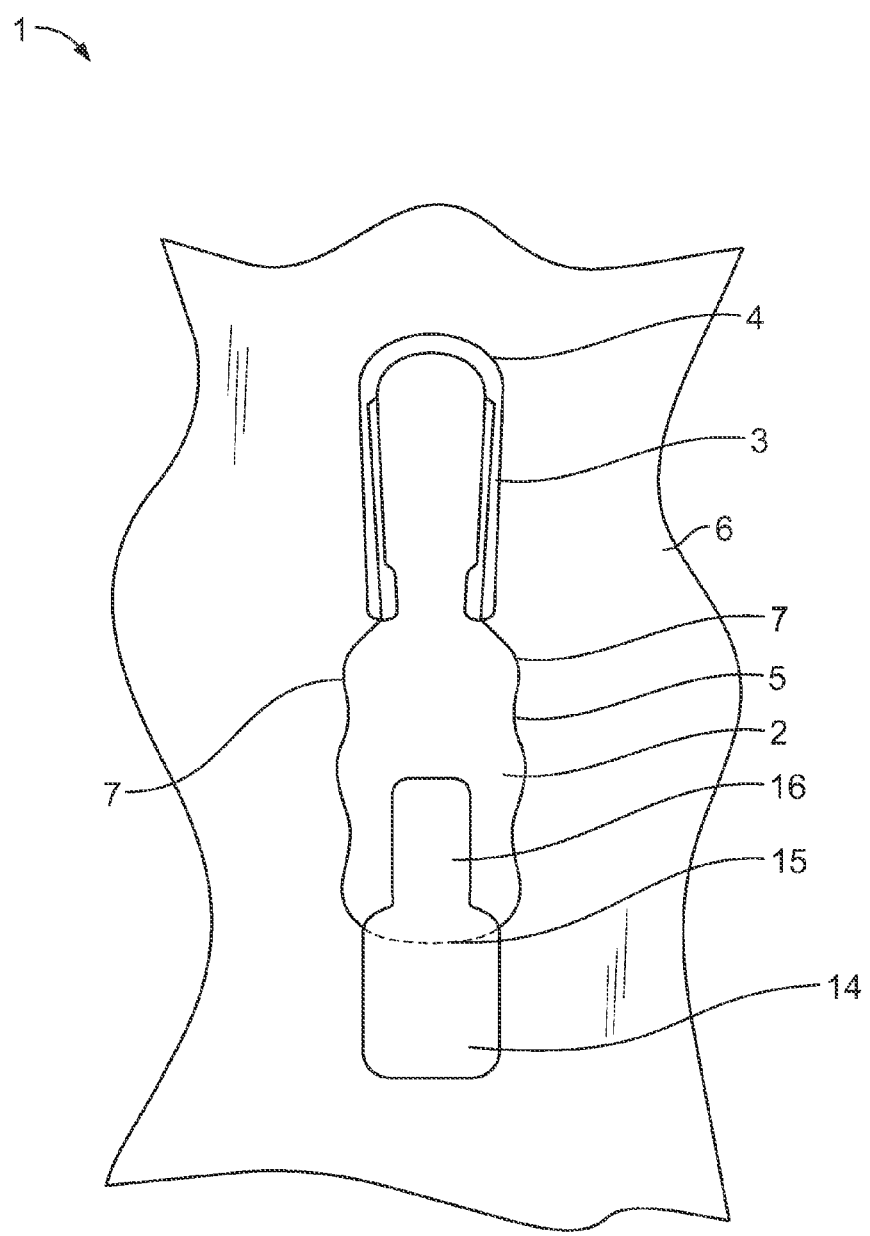
FIG. 1 shows a drape according to the disclosure in the region of a first opening.

FIG. 1 illustrates a section of a drape 1 according to the disclosure in the region of a first opening 2. In this exemplary embodiment, the drape 1 includes a thin, transparent film 6, which is preferably made of polyethylene or a suitable different plastic. A first opening 2 has been introduced into the film 6, on the edge of which opening a first attachment device and a second attachment device are connected to the drape.

The first attachment device is embodied as a U-shaped holder 3 and adhesively bonded, welded or connected in any other form to the film 6 along a first part 4 of the edge 5 of the first opening 2. Geometry and material of the U-shaped holder 3 are selected such that the two ends of the holder can be pulled apart without exerting too much force such that the holder can easily be plugged onto a counterpart (e.g. in the form of a component of a surgical microscope) and is held on the counterpart by a restoring force.

The second attachment device is embodied as a plate 14 and adhesively bonded, welded or connected in any other suitable form to the film along a second part 15 of the edge 5 of the first opening 2. Part of the plate 14 is embodied as connection element 16 and extends from the second part 15 of the edge 5 into the first opening 2. The function of the connection element 16 will still be explained in more detail in the following text.

Together, the first part 4 and the second part 15 of the edge 5 extend over less than the totality of the edge 5 of the first opening 2. Freely movable sections 7 of the edge 5 are respectively arranged between the first part 4 and the second part 15 such that the U-shaped holder 3 and the plate 14 can be positioned relative to one another as desired. As a result, an assembly of the drape 1 on the surgical microscope is simplified. On the edge 5, it is particularly preferable for spring elements, for example in the form of elastic bands, to be attached on the film 6 of the drape along the freely movable sections 7 between the U-shaped holder 3 and the plate 14, by which spring elements an opening area of the first opening 2 is kept small when the drape is affixed to the surgical microscope.

Figure 2:
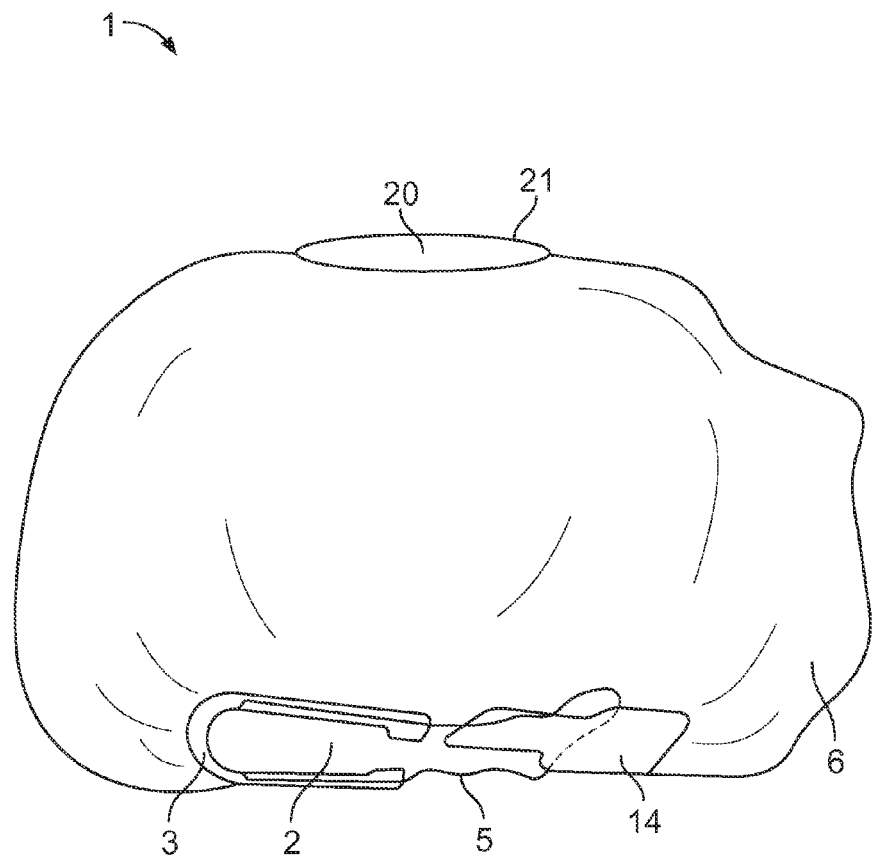
FIG. 2 shows a perspective view of the drape from FIG. 1.

The drape 1 is illustrated in a perspective view in FIG. 2. In this exemplary embodiment, the drape 1 has a second opening 20, on the edge of which an elastic element in the form of an elastic band 21 is attached to the film 6. An opening area of the second opening 20 can be enlarged by stretching the elastic band 21 such that the drape 1 can easily be pulled or placed over a surgical microscope.

Figure 3:
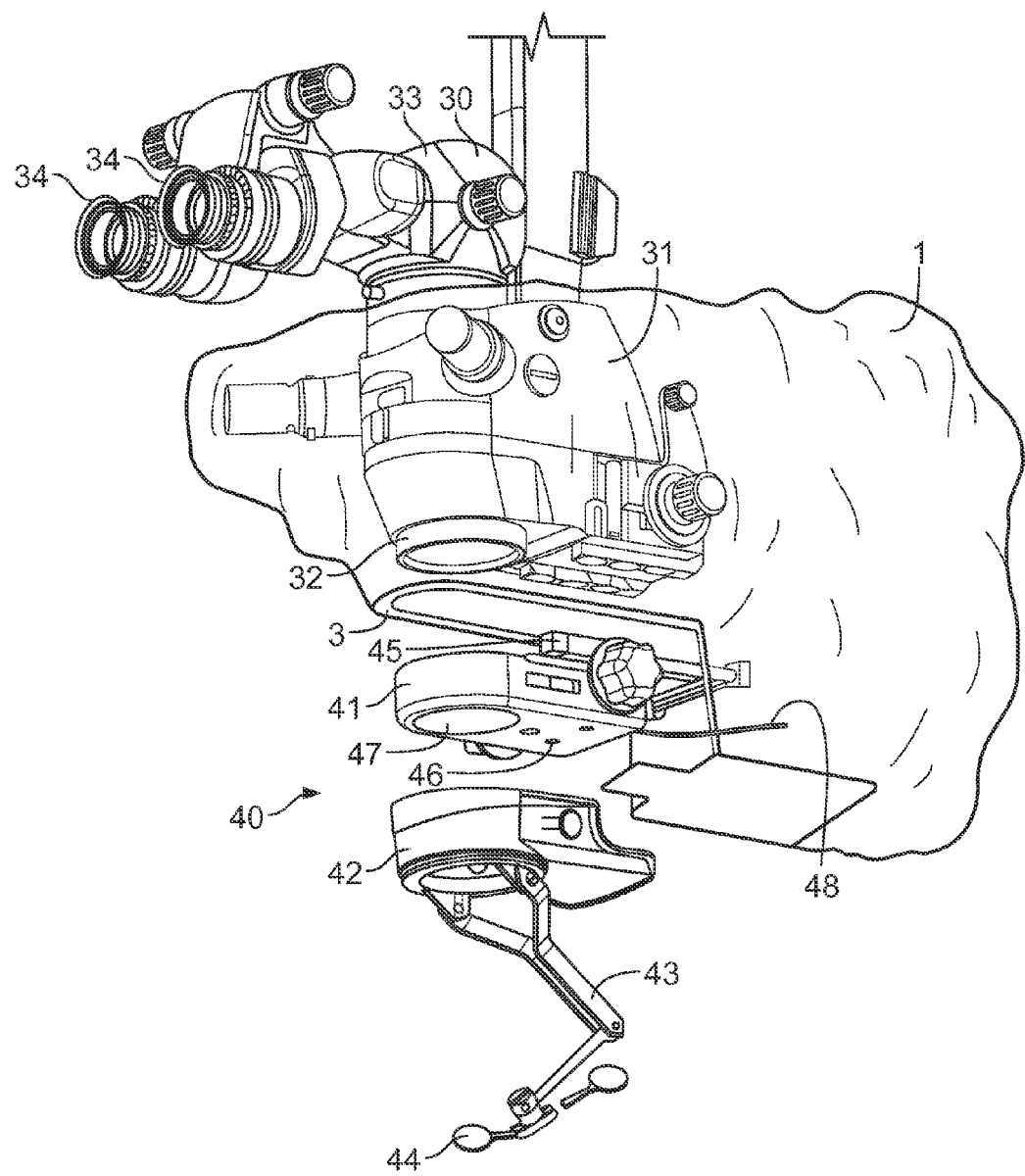
FIG. 3 shows an exploded drawing of a surgical microscope with a drape according to the disclosure.

FIG. 3 illustrates a surgical microscope 30 with a drape 1 in an exploded drawing. The surgical microscope 30 includes a plurality of components. A first component of the surgical microscope 30 contains a microscope body 31 with a main objective 32, a tube 33 and eyepieces 34. Below the main objective 32, a second component of the surgical microscope 30 in the form of an attachment apparatus 40 is arranged on the main body 31. The attachment apparatus 40 includes a focusing apparatus 41 and a covering cap 42, on which a holding arm 43 with a fundus lens 44 is attached.

The focusing apparatus 41 contains a guide body 45, which is attached to the main body 31 of the surgical microscope. A housing 46 of the focusing apparatus is connected to the guide body such that it can be displaced in one direction by translation. As a result of this, it is optionally possible to insert an optical system of the focusing apparatus, arranged in the housing 46, into an observation beam path of the surgical microscope or to remove it from the observation beam path.

The covering cap 42 is clamped to the housing 46 of the focusing apparatus 41, or attached thereto in another detachable fashion. Arranged on the covering cap 42 is a holding arm 43, which has a mount for the fundus lens 44. Covering cap 42 and holding arm 43 are preferably made of materials that allow sterilization of the device in an autoclave or with the aid of other conventional methods.

When the covering cap 42 with the holding arm 43 and the fundus lens 44 is attached to the housing 46 of the focusing apparatus 41, these elements together form a component of the surgical microscope which can be put into at least two work positions relative to the microscope body 31 by displacement along the guide body 45. In a first work position, the optical system 47 of the focusing apparatus 41 and the fundus lens 44 are arranged in an observation beam path of the surgical microscope. In this position it is possible to observe an eye background (fundus) of a patient eye using the surgical microscope. In a second work position, the aforementioned optical elements have been removed from the observation beam path such that a front section of the patient eye can be examined using the surgical microscope.

Certain components of the surgical microscope 30 are covered by a drape 1 in order to keep these sterile. Here, in the region of the first opening 2, the drape 1 is connected to a first, fixed component of the surgical microscope via the U-shaped holder 3. In this exemplary embodiment, the U-shaped holder 3 has, for this purpose, been inserted into a groove which is formed between the microscope body 31 and the guide body 45 of the focusing apparatus 41. However, without loss of generality, the drape could also be connected to the surgical microscope via a groove that was introduced into the microscope body 31 for this purpose. In a further exemplary embodiment (not illustrated), the drape is affixed to the microscope body or another fixed component of the surgical microscope by a first attachment device in the form of an adhesive strip.

Figure 7:
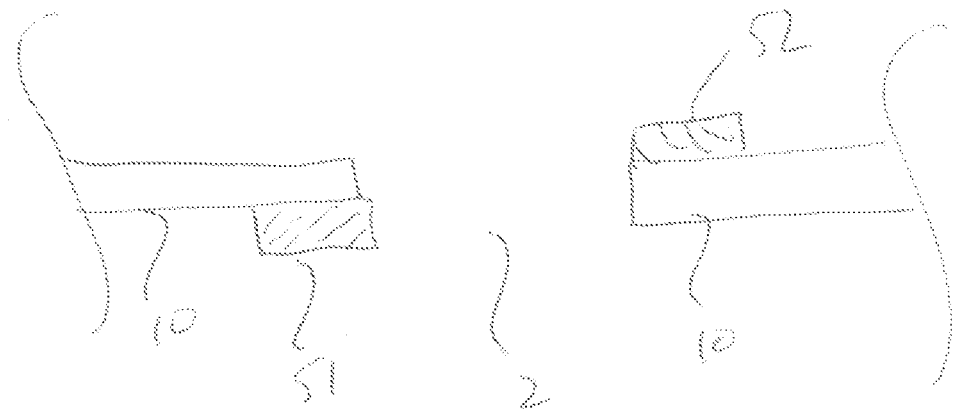
FIG. 7 shows the drape with each of the first and second attachment devices in the form of a detachable adhesive connection.
Figure 8:
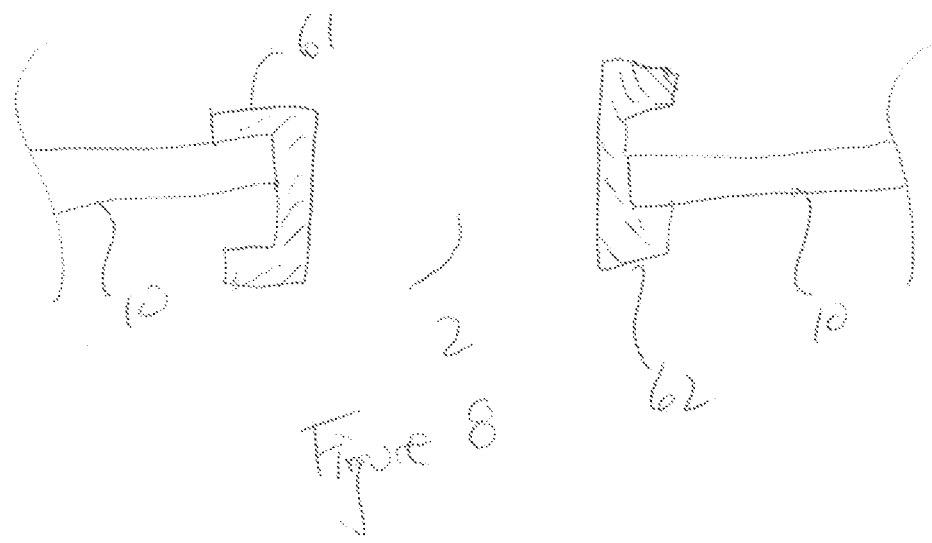
FIG. 8 shows the drape with each of the first and second attachment devices in the form of a clamping device.

Via the second attachment device, which is embodied as a plate 14, the drape is additionally connected to a second, movable component of the surgical microscope 30, the second component in this exemplary embodiment being formed by the housing 46 of the focusing apparatus 41 and the covering cap 42 with the holding arm 43 and the fundus lens 44. To this end, the connection element 16, embodied in the shape of a tongue, of the plate 14 has been inserted into a gap between the housing 46 of the focusing apparatus 41 and the covering cap 42. In further exemplary embodiments (not illustrated), the connection element is connected to a movable component of the surgical microscope via an adhesive connection, a hook-and-loop fastener, a clamping device, a push-button or any other cohesive, force-fit or interlocking detachable connection. FIG. 7 shows an embodiment in which the first and second attachments devices are detachable adhesive connections 51 and 52, respectively. FIG. 8 shows an embodiment in which the first and second attachments devices are clamping devices 61 and 62, respectively.

When the focusing apparatus 40 is moved along the guide body 45, the drape 1 is also carried along in the region of the plate 14. This prevents the drape 1 from folding together in an uncontrolled manner in this region and from penetrating into a workspace of the operator below the surgical microscope or into the observation beam path. As a result of embodying the connection element as a plate 14, a solid barrier is created between the interior of the drape and a workspace below the surgical microscope. This reduces the risk of connection lines 48 of the movable component reaching the workspace in the case of a displacement of the component or of an operator of the surgical microscope inadvertently touching the non-sterile connection lines 48 during surgery.

Figure 4:
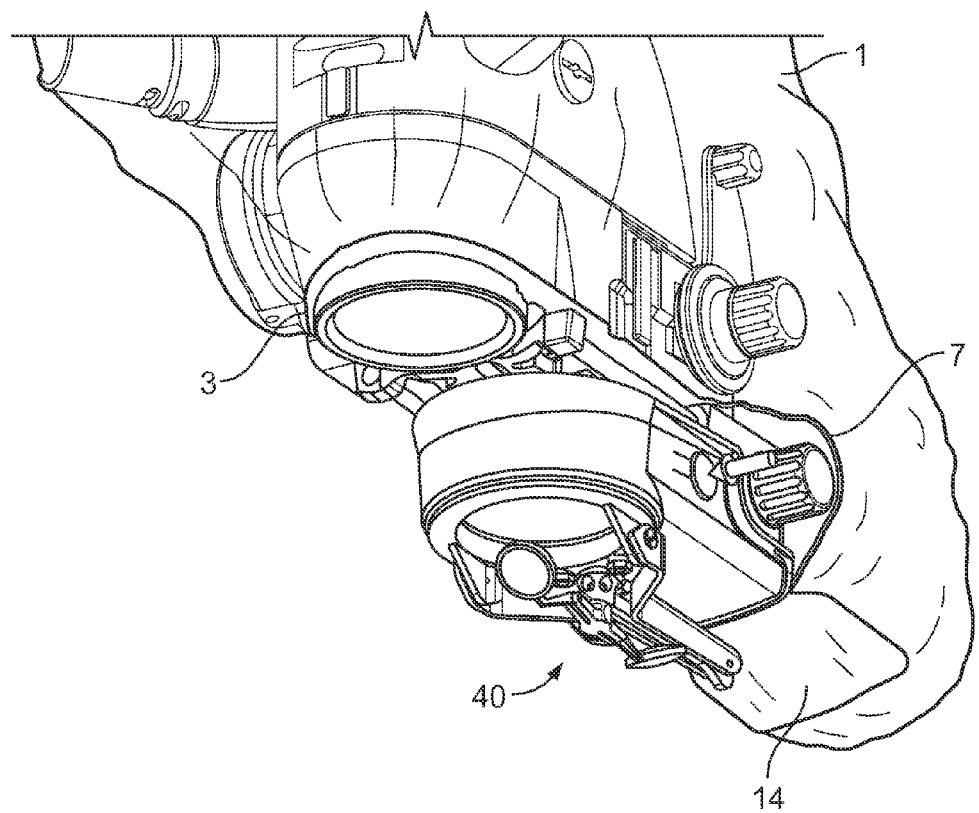
FIG. 4 shows a perspective view of a surgical microscope with a drape according to the disclosure.
Figure 5:
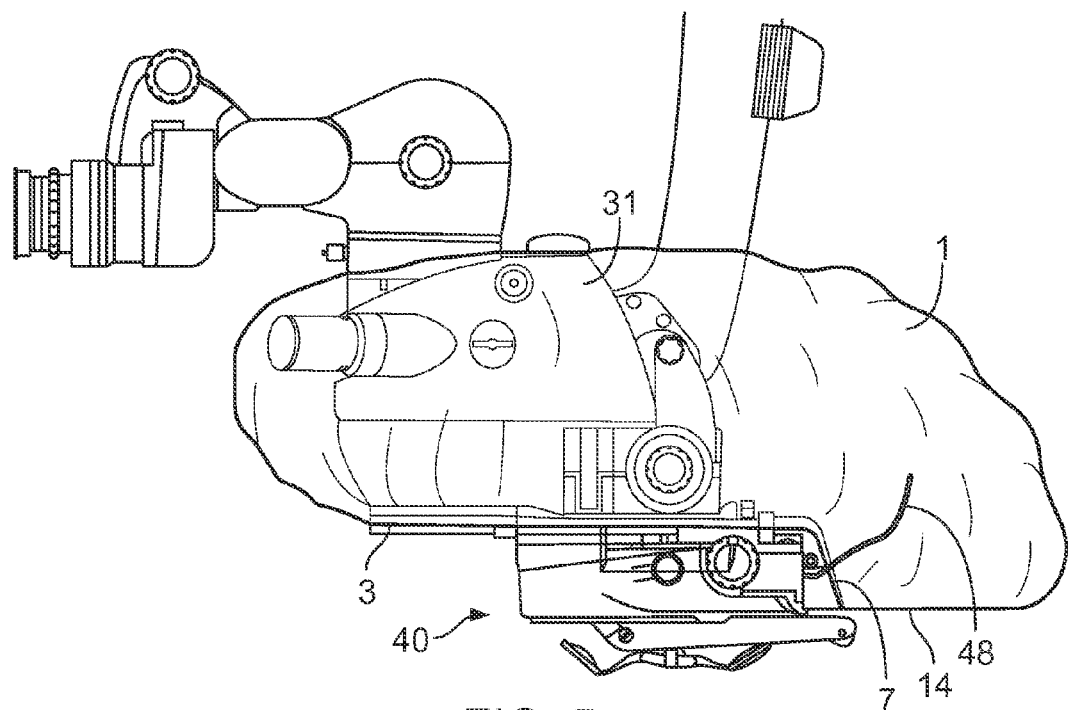
FIG. 5 shows a surgical microscope in a first working position with a drape according to the disclosure.
Figure 6:
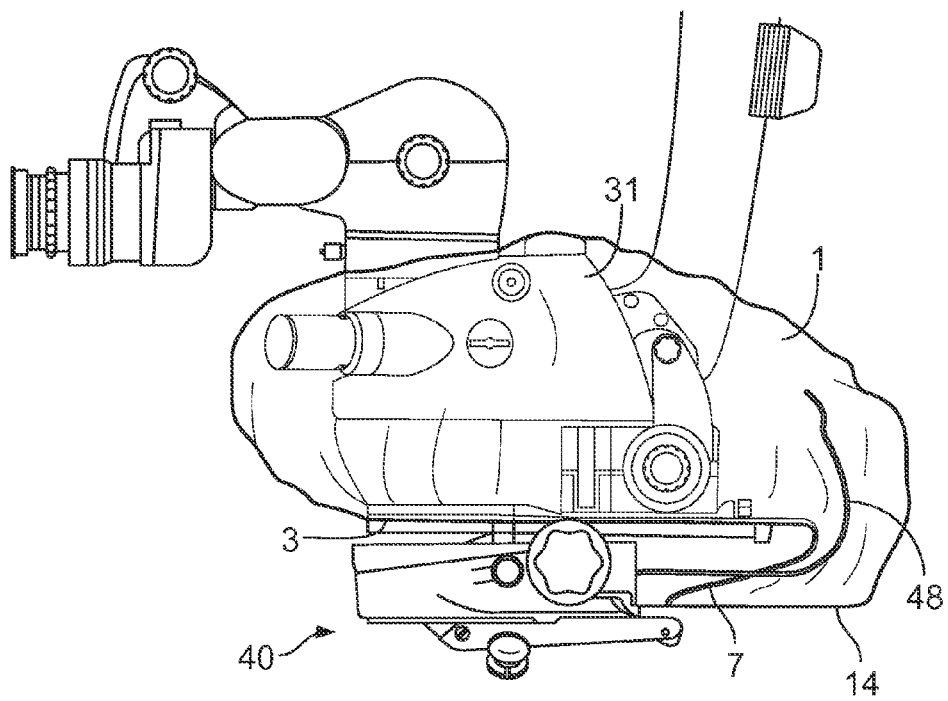
FIG. 6 shows the surgical microscope with drape from FIG. 5 in a second working position.

FIG. 4 illustrates the surgical microscope 30 with drape 1 in a first work position. Here, the attachment device 40 has been pivoted out of an observation beam path of the surgical microscope. In the free sections 7 of the first opening 2 between the U-shaped holder 3 and the plate 14, the edge 5 has a strengthened design compared to an average thickness of the film 6 and therefore it has a greater rigidity. It is particularly preferred for the free sections 7 of the first opening to have an elastic design. This ensures that the assembled drape is held closely against the surgical microscope. In a further exemplary embodiment (not illustrated), additional stiffening elements and/or additional spring-elastic elements, for example in the form of an elastic band, are arranged on the free sections, as a result of which a position of the drape on the surgical microscope in the region of the first opening is improved further, and tight resting on the surgical microscope is ensured. In FIG. 5 and FIG. 6, the surgical microscope is illustrated in different work positions in a lateral view.

What is claimed is:

1. An article, comprising:
   a drape having a first opening with an edge;
   a first attachment device directly overlapping and extending along a first section of the edge of the first opening, the first attachment device configured to affix the drape to a surgical microscope; and
   a second attachment device directly overlapping and extending along a second section of the edge of the first opening, the second attachment device configured to affix the drape on the surgical microscope,
   wherein:
   the edge of the first opening has a first freely movable section and a second freely movable section, both the first and the second freely movable sections are between the first and second sections of the edge of the first opening,
   a first end of the first section of the edge of the first opening adjoins the first freely movable section, a second end of the first section of the edge of the first opening adjoins the second freely movable section,
   a first end of the second section of the edge of the first opening adjoins the first freely movable section, and a second end of the second section of the edge of the first opening adjoins the second freely movable section, and
   the first and second freely movable sections are configured to allow a position of the first attachment device to be varied relative to the second attachment device.

2. The article of claim 1, wherein the first attachment device comprises a detachable adhesive connection.

3. The article of claim 1, wherein the first attachment device comprises a clamping device configured to attach the drape to the surgical microscope in a region of the first section of the edge of the first opening.

4. The article of claim 3, wherein the clamping device comprises a U-shaped holder configured to be inserted into a groove on the surgical microscope.

5. The article of claim 1, wherein the second attachment device comprises a rigid connection element configured to affix the drape to the surgical microscope.

6. The article of claim 5, wherein the rigid connection element comprises a plate.

7. The article of claim 1, wherein the first attachment device comprises a clamping device.

8. The article of claim 1, wherein the first and second sections of the edge together extend over less than a totality of the edge of the first opening.

9. The article of claim 1, wherein the first attachment device comprises a detachable adhesive connection, and the second attachment device comprises a detachable adhesive connection.

10. The article of claim 1, wherein the first attachment device comprises a clamping device, and the second attachment device comprises a clamping device.

11. The article of claim 10, wherein the clamping device of the first attachment device is configured to attach the drape to a housing of the surgical microscope in a first region of the first opening, and the clamping device of the second attachment device is configured to attach the drape to the housing of the surgical microscope in a second region of the first opening.

12. The article of claim 1, further comprising an elastic element attached to an edge of a second opening of the drape, wherein the elastic element is configured to exert an elastic force on the edge of the second opening.

13. The article of claim 12, wherein the elastic element is configured to exert an elastic force on at least two points of the edge of the second opening.

14. The article of claim 1, wherein a third section of the edge of the first opening of the drape is one of the first and second freely movable sections of the edge of the first opening extending between the first and second sections of the edge of the first opening of the drape, the first attachment device does not contact the third section of the edge of the first opening of the drape, and the second attachment device does not contact the third section of the edge of the first opening of the drape.

15. The article of claim 1, wherein the first attachment device and the second attachment device do not directly contact each other.

16. The article of claim 1, wherein the two freely movable sections of the drape do not contact portions of the first attachment device between the first and second ends of the first section, and portions of the second attachment device between the first and second ends of the second section.

17. The article of claim 1, wherein a first end of the first freely movable section contacts the first end of the first section, and a second end of the first freely movable section contacts the first end of the second section.

18. A system, comprising:
a surgical microscope;
a drape having a first opening with an edge;
a first attachment device directly overlapping and extending along a first section of the edge of the first opening; and
a second attachment device directly overlapping and extending along a second section of the edge of the first opening, wherein:
the first attachment device affixes the drape to the surgical microscope;
the second attachment device affixes the drape on the surgical microscope;
a third section and a fourth section of the edge of the first opening of the drape both extend between the first and second sections of the edge of the first opening of the drape;
a first end of the first section of the edge of the first opening adjoins the third section, a second end of the first section of the edge of the first opening adjoins the fourth section,
a first end of the second section of the edge of the first opening adjoins the third section, and a second end of the second section of the edge of the first opening adjoins the fourth section,
the third and fourth sections are configured to allow a position of the first attachment device to be varied relative to the second attachment device;
the first attachment device does not contact the third section of the edge of the first opening of the drape; and
the second attachment device does not contact the third section of the edge of the first opening of the drape.

19. The system of claim 18, wherein the first attachment device comprises a detachable adhesive connection.

20. The system of claim 18, wherein the first attachment device comprises a clamping device which attaches the drape to the surgical microscope in a region of the first opening.

21. The system of claim 18, further comprising an elastic element attached to an edge of a second opening of the drape, wherein the elastic element is configured to exert an elastic force on the edge of the second opening.

22. The system of claim 21, wherein the elastic element is configured to exert an elastic force on at least two points of the edge of the second opening.

23. The system of claim 18, wherein at least a portion of the third section extends in a direction perpendicular to the first and second sections.

24. An article, comprising:
a drape having a first opening with an edge;
a first attachment device directly overlapping and extending along a first section of the edge of the first opening, the first attachment device comprises a clamping device configured to attach the drape to a surgical microscope in a region of the first section of the edge of the first opening; and
a second attachment device directly overlapping and extending along a second section of the edge of the first opening, the second attachment device comprises a plate configured to affix the drape on the surgical microscope,
wherein:
the edge of the first opening has a first freely movable section and a second freely movable section, both the first and the second freely movable sections are between the first and second sections of the edge of the first opening,
a first end of the first section of the edge of the first opening adjoins the first freely movable section, a second end of the first section of the edge of the first opening adjoins the second freely movable section,
a first end of the second section of the edge of the first opening adjoins the first freely movable section, and a second end of the second section of the edge of the first opening adjoins the second freely movable section, and the first and second freely movable sections are configured to allow a position of the first attachment device to be varied relative to the second attachment device.

\* \* \* \* \*